(12) United States Patent
Kilgrow et al.

(10) Patent No.: US 11,583,425 B2
(45) Date of Patent: Feb. 21, 2023

(54) ENDOPROSTHESIS DELIVERY SYSTEM WITH IMPROVED RETRACTION

(71) Applicant: W. L. Gore & Associates, Inc., Newark, DE (US)

(72) Inventors: Bret J. Kilgrow, Flagstaff, AZ (US); Larry J. Kovach, Flagstaff, AZ (US); Brandon C. Short, Bellemont, AZ (US); Anna F. Timbie, Sunnyvale, CA (US)

(73) Assignee: W. L. Gore & Associates, Inc., Newark, DE (US)

( * ) Notice: Subject to any disclaimer, the term of this patent is extended or adjusted under 35 U.S.C. 154(b) by 1054 days.

(21) Appl. No.: 16/266,349

(22) Filed: Feb. 4, 2019

(65) Prior Publication Data

US 2019/0167459 A1    Jun. 6, 2019

Related U.S. Application Data

(63) Continuation of application No. 14/826,040, filed on Aug. 13, 2015, now Pat. No. 10,195,064.

(60) Provisional application No. 62/038,000, filed on Aug. 15, 2014.

(51) Int. Cl.
*A61F 2/966* (2013.01)

(52) U.S. Cl.
CPC ...... *A61F 2/966* (2013.01); *A61F 2002/9665* (2013.01)

(58) Field of Classification Search
CPC .............. A61F 2/966; A61F 2002/9665; A61F 2002/9505; A61F 2002/075; A61F 2/95
See application file for complete search history.

(56) References Cited

U.S. PATENT DOCUMENTS

| 6,224,627 | B1 | 5/2001 | Armstrong |
| 6,264,689 | B1 | 7/2001 | Colgan et al. |
| 6,315,792 | B1 | 11/2001 | Armstrong et al. |

(Continued)

FOREIGN PATENT DOCUMENTS

| DE | 102006053748 B3 | 4/2008 |
| EP | 2957953 A1 | 12/2015 |

(Continued)

OTHER PUBLICATIONS

International Preliminary Report on Patentability received for PCT Patent Application No. PCT/US2015/045227, dated Mar. 2, 2017, 7 pages.

(Continued)

*Primary Examiner* — Anh T Dang

(57) ABSTRACT

The present disclosure includes an endoprosthesis delivery system comprising an elongate member, such as a catheter, an endoprosthesis, and an end cap having one or more protrusions extending therefrom. The protrusions may assist in retraction of end cap into an outer sheath, such as an introducer sheath. In some examples, the protrusion includes fins. In some embodiments, the endoprosthesis delivery system further includes a covering member disposed about the endoprosthesis. The protrusions may support the covering member, which may extend beyond the distal end of the endoprosthesis and onto the end cap. In some embodiments, the end cap comprises a tapered profile, which may assist in retraction of the catheter tip and end cap into an outer sheath.

33 Claims, 6 Drawing Sheets

(56) References Cited

U.S. PATENT DOCUMENTS

| | | |
|---|---|---|
| 6,322,586 B1 | 11/2001 | Monroe |
| 6,355,060 B1 | 3/2002 | Lenker et al. |
| 6,607,551 B1 | 8/2003 | Sullivan |
| 6,767,338 B2 | 7/2004 | Hawk et al. |
| 6,790,221 B2 | 9/2004 | Monroe et al. |
| 7,004,962 B2 | 2/2006 | Stinson |
| 8,070,790 B2 | 12/2011 | Berra |
| 8,756,789 B2 | 6/2014 | Sokel |
| 10,195,064 B2 | 2/2019 | Kilgrow et al. |
| 2002/0005264 A1 | 1/2002 | McGary |
| 2002/0193868 A1* | 12/2002 | Mitelberg ............... A61F 2/915 623/1.35 |
| 2003/0144670 A1 | 7/2003 | Pavcnik et al. |
| 2004/0193243 A1 | 9/2004 | Mangiardi |
| 2006/0004439 A1 | 1/2006 | Spenser et al. |
| 2006/0276872 A1 | 12/2006 | Arbefeuille |
| 2007/0100422 A1 | 5/2007 | Shumer |
| 2009/0099637 A1* | 4/2009 | Barthold ................... A61F 2/95 623/1.11 |
| 2009/0276027 A1 | 11/2009 | Glynn |
| 2009/0281617 A1 | 11/2009 | Cottone et al. |
| 2010/0030255 A1* | 2/2010 | Berra ....................... A61F 2/966 623/1.13 |
| 2011/0218607 A1* | 9/2011 | Arbefeuille ............. A61F 2/844 623/1.11 |
| 2011/0224774 A1 | 9/2011 | Silveira |
| 2012/0078237 A1 | 3/2012 | Wang et al. |
| 2012/0259403 A1 | 10/2012 | Hendriksen et al. |
| 2013/0204344 A1* | 8/2013 | Tatalovich .............. A61F 2/962 623/1.12 |
| 2013/0268051 A1 | 10/2013 | Atlani |
| 2013/0297010 A1 | 11/2013 | Bishop et al. |
| 2014/0094895 A1 | 4/2014 | Core et al. |
| 2014/0148889 A1 | 5/2014 | Deshmukh |

FOREIGN PATENT DOCUMENTS

| | | |
|---|---|---|
| JP | 2002-518086 | 6/2002 |
| JP | 2003-500104 | 1/2003 |
| JP | 2004-501672 | 1/2004 |
| JP | 2006-521885 | 9/2006 |
| JP | 2011-519608 | 7/2011 |
| WO | WO-199965420 | 12/1999 |
| WO | WO-2000071058 | 11/2000 |
| WO | WO-2001051114 | 7/2001 |
| WO | WO-2004091452 | 10/2004 |
| WO | WO-2007059293 A1 | 5/2007 |
| WO | WO-2009134801 | 11/2009 |
| WO | WO-2012104763 | 8/2012 |
| WO | 2014/158958 A1 | 10/2014 |

OTHER PUBLICATIONS

International Search Report and Written Opinion received for PCT Patent Application No. PCT/US2015/045227, dated Nov. 5, 2015, 9 pages.

International Search Report and Written Opinion from PCT/US2015/045227, dated Nov. 5, 2015, 10 pages.

* cited by examiner

ENDOPROSTHESIS DELIVERY SYSTEM WITH IMPROVED RETRACTION

CROSS-REFERENCE TO RELATED APPLICATION

This application is a continuation of U.S. patent application Ser. No. 14/826,040, filed Aug. 13, 2015, now U.S. Pat. No. 10,195,064, issued Feb. 5, 2019, which claims the benefit of U.S. Provisional Application 62/038,000, filed Aug. 15, 2014, both of which are incorporated herein by reference in their entireties for all purposes.

FIELD

The present disclosure generally relates to endoprostheses for treating diseases of the vasculature and similar anatomies, and more particularly, to endoprosthesis delivery systems with at least one end cap proximal to a distal tip of the endoprosthesis delivery system.

BACKGROUND

Many endoprosthesis, such as, for example, stent-grafts, are constructed to reinforce, replace, bridge, or otherwise treat a part of a blood vessel. An endoprosthesis may guide blood flow through a lumen defined by a generally tubular interior of such a vessel. Other tubular endoprostheses are designed for use in other body regions, for example, the esophagus, ureters, gastrointestinal tract and various ducts. In many cases, endoprostheses are constrained within a covering member or sheath and delivered to the body region requiring treatment on the end of an elongate member. When the covering member is removed, as during deployment, the devices are expanded under force or self-expand to assume a larger diameter. After delivery and deployment of the endoprosthesis, the elongate member used to delivery and deploy the endoprosthesis is retracted into a tubular outer shaft and removed from the body. In some instances, it may be difficult to properly align the elongate member and endoprosthesis with the outer shaft, causing difficulties in retraction. Thus, improved endoprosthesis delivery systems are desirable.

SUMMARY

Endoprosthesis delivery systems in accordance with the present disclosure can comprise an elongate member, an endoprosthesis comprising a distal end, an end cap having a cylindrical body, wherein the end cap is coupled to the elongate member adjacent to the distal end of the endoprosthesis, and a covering member surrounding a portion of the endoprosthesis, wherein a distal end of the covering member extends beyond the distal end of the endoprosthesis, and wherein a proximal end of the end cap comprises a tapered profile.

Endoprosthesis delivery systems in accordance with the present disclosure can further comprise a tip adjacent a distal end of the end cap. The tip can have a diameter larger than a diameter of the end cap. The tip and end cap can be integrated. The end cap can comprise a region of reduced diameter located between the proximal end and the distal end of the end cap. The distal end of the covering member can be positioned in the region of reduced diameter. The proximal end of the tip can be spaced apart from the distal end of the end cap. The distal end of the covering member can be positioned between the proximal end of the tip and the distal end of the end cap. The proximal end of the end cap can comprise a fin. The fin can be angled relative to a longitudinal axis of the end cap, and the fin can fold upon retraction of the end cap into the catheter The covering member can comprise a plurality of knit fibers, which can be woven about an exterior surface of the endoprosthesis and constrain the endoprosthesis in a constrained configuration. The delivery system can further comprise a pull line coupled to the covering member. The endoprosthesis can be a stent or stent-graft or similar device. The elongate member can be a guide wire. The delivery system can further comprise a catheter.

BRIEF DESCRIPTION OF THE DRAWINGS

The features and advantages of the present disclosure will become more apparent from the detailed description set forth below when taken in conjunction with the drawings, wherein.

DETAILED DESCRIPTION

Figure 1:
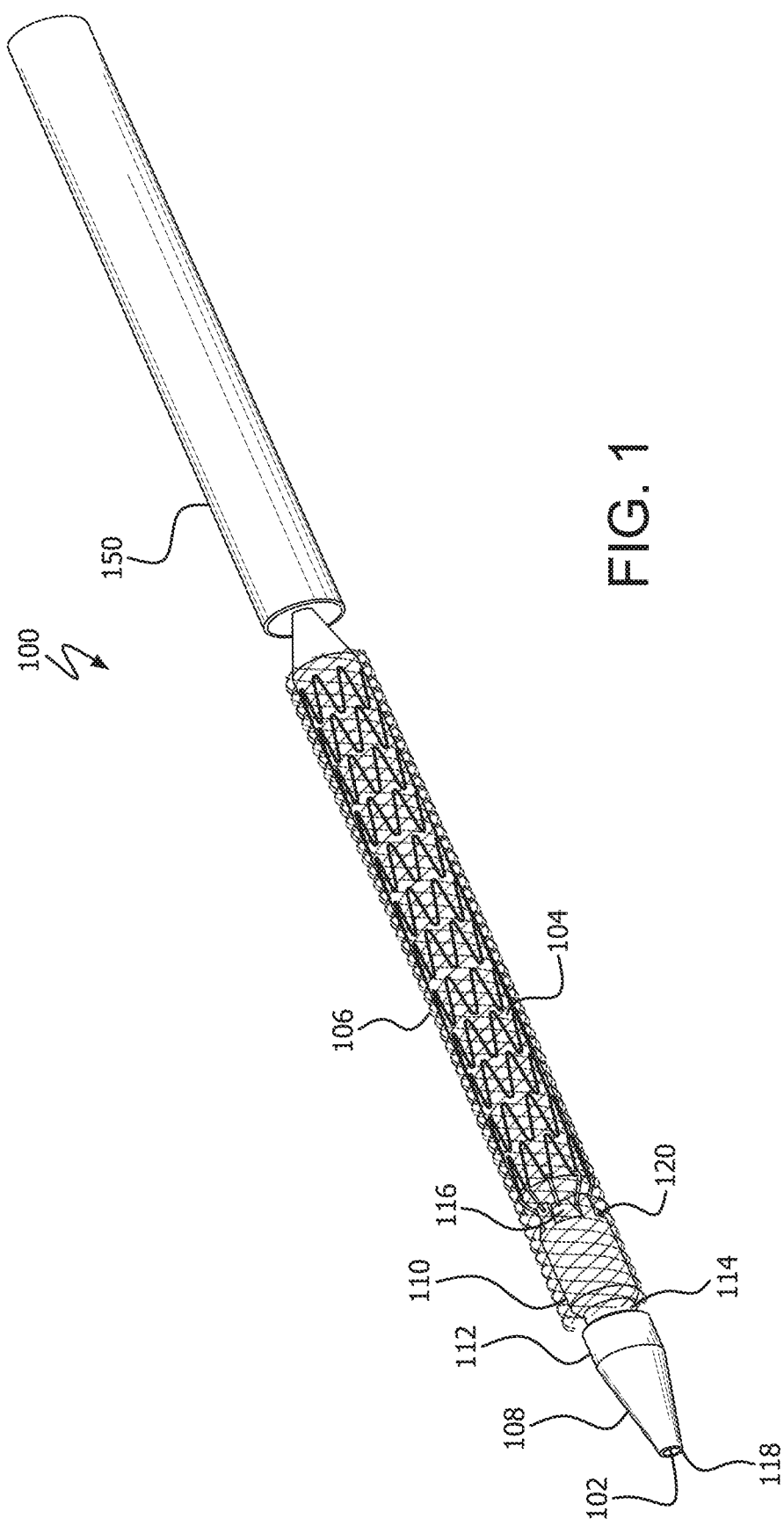
FIG. 1 illustrates a perspective view of an endoprosthesis delivery system in accordance with the present disclosure.
Figure 2:
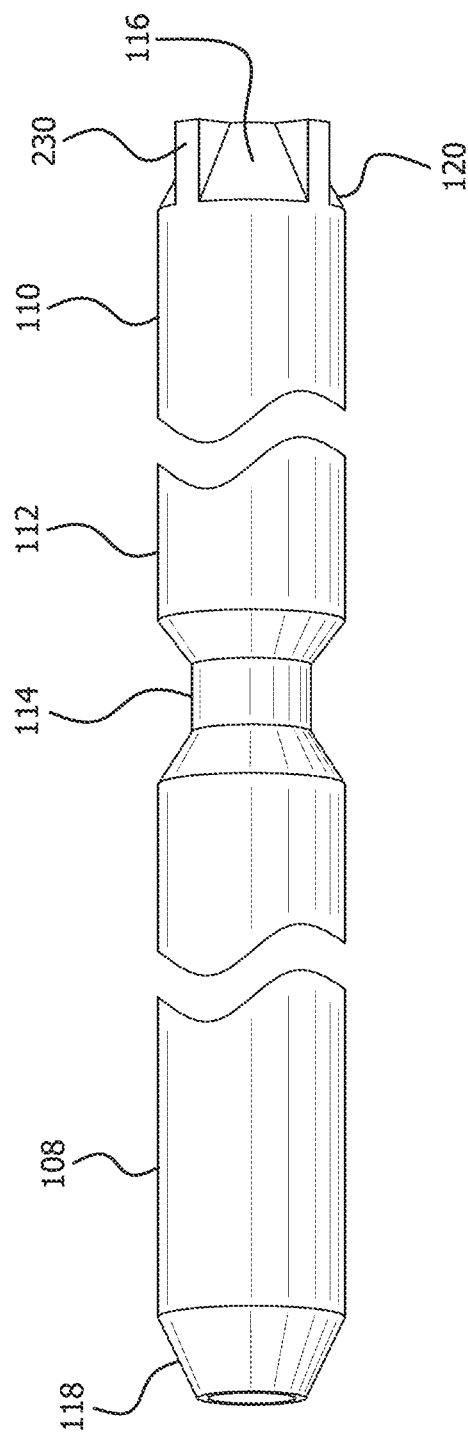
FIG. 2 illustrates a perspective view of a combined tip and end cap of an endoprosthesis delivery system in accordance with the present disclosure.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "endoprosthetic device," "endoprosthesis," "vascular device," and the like can refer, throughout the specification and in the claims, to any medical device capable of being implanted and/or deployed within a body lumen. In various instances, an endoprosthesis can comprise a stent, a stent-graft, graft, a filter, an occluder, a balloon, a lead, and energy transmission device, a deployable patch, an indwelling catheter, and the like.

In addition, throughout this specification and claims, the delivery systems described herein can, in general, include an endoprosthesis constrained by a "covering member" or "sheath." The covering member or sheath can, in various embodiments, comprise a sheet of material that is fitted about an endoprosthesis. The covering member or sheath can, in various embodiments, comprise a plurality of knitted fibers located about the endoprosthesis. These fibers can, for example, comprise a woven warp knit or knit-braid, as described in U.S. Pat. No. 6,315,792 to Armstrong et al., issued Nov. 13, 2001, entitled "Remotely removable covering and support," which is incorporated herein, in its entirety, by reference. The covering member can be coupled to a pull line extending down the length of the catheter, which a clinician can pull to facilitate uncovering the endoprosthesis.

For example, a covering member comprising a plurality of fibers can be coupled to a pull line, which a clinician can pull to unravel the plurality of fibers. Thus, the covering member can be characterized as "unzipped", in that the pull line causes the covering member to open or unzip along a straight line. In addition, in various embodiments, a covering member can be unzipped, first, along a proximal vector and, second, along a distal vector. In various embodiments, a covering member can be unzipped along a longitudinal vector running substantially parallel to the longitudinal axis of an elongate member.

As used throughout the specification and in the claims, the term "elongate member" can refer to a shaft-like structure such as a catheter, guidewire, or the like. In various embodiments, an endoprosthesis can be mounted or loaded on a catheter, also referred to herein as an inner shaft.

As used throughout the specification and in the claims, the term "outer shaft" can refer to a tubular element comprising a lumen, into which the endoprosthesis in a constrained diameter may be inserted and delivered into the body of a patient. Outer shafts can comprise, for example, an introducer sheath, among other suitable constructs.

Further, the term "distal" refers to a relative location that is farther from a location in the body at which the medical device was introduced. Similarly, the term "distally" refers to a direction away from a location in the body at which the medical device was introduced.

The term "proximal" refers to a relative location that is closer to the location in the body at which the medical device was introduced. Similarly, the term "proximally" refers to a direction towards a location in the body at which the medical device was introduced.

With continuing regard to the terms proximal and distal, this disclosure should not be narrowly construed with respect to these terms. Rather, the devices and methods described herein may be altered and/or adjusted relative to the anatomy of a patient.

As used herein, the term "constrain" may mean (i) to limit expansion, occurring either through self-expansion or expansion assisted by a device, of the diameter of an expandable implant, or (ii) to cover or surround an expandable implant (e.g., for storage or biocompatibility reasons and/or to provide protection to the expandable implant and/or the vasculature).

As used herein, the term "integral" refers to elements or components which are connected and/or coupled to each other such that they form a single physical object or structure.

In various embodiments, an endoprosthesis delivery system can comprise an elongate member, such as a catheter, an endoprosthesis, a covering member disposed about the endoprosthesis, a tip, and an end cap with a distally-tapered profile. The covering member can extend beyond an end of the endoprosthesis and on to the tip and/or end cap. The tip and/or end cap can comprise a region of reduced diameter. Further, the distal end of the covering member can terminate within the region of reduced diameter.

With initial reference to FIG. 1, an endoprosthesis delivery system 100 can comprise, in various instances, an elongate member 102 onto which an endoprosthesis 104 is mounted. Elongate member 102 and endoprosthesis 104 can be surrounded by an outer shaft 150, such as an introducer sheath, or other tubular shaft member. In various instances, elongate member 102 and endoprosthesis 104 are passed through outer shaft 150 to deliver endoprosthesis 104 to a desired treatment area of a patient.

In various instances, endoprosthesis 104 comprises a compressible medical device. For example, in various embodiments, endoprosthesis 104 comprises a stent or stent-graft. Conventional stent-grafts are designed to dilate from their delivery diameter, through a range of intermediary diameters, up to a maximal, pre-determined functional diameter, and generally comprise one or more stent components with one or more graft members covering all or part of the inner and/or outer surfaces of the stent.

In various embodiments, endoprosthesis 104 comprises one or more stent components made of nitinol and a graft member made of ePTFE. However, and as discussed below, any suitable combination of stent component(s) and graft member(s) is within the scope of the present disclosure.

For example, stent components can have various configurations such as, for example, rings, cut tubes, wound wires (or ribbons) or flat patterned sheets rolled into a tubular form. Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly(caprolactones), poly(lactic/glycolic acid) polymers, poly(hydroxybutyrates) and poly(orthoesters). Any expandable stent component configuration which can be delivered by a catheter is in accordance with the present disclosure.

Potential materials for graft members include, for example, expanded polytetrafluoroethylene (ePTFE), polyester, polyurethane, fluoropolymers, such as perfluoroelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers or aramid fibers. Further, a graft may comprise a class of polyesters such as polyethylene terephthalate and polyaramids, polyfluorocarbons such as polytetrafluoroethylene (PTFE) with and without copolymerized hexafluoropropylene, and porous or nonporous polyurethanes. Any graft member that can be delivered by a catheter is in accordance with the present disclosure.

In various instances, system 100 further comprises a covering member 106 surrounding at least a portion of endoprosthesis 104 and maintaining endoprosthesis 104 in a constrained configuration. For example, covering member 106 can comprise a plurality of woven warp knit or knit-braid fibers. In such embodiments, the distal and/or proximal end regions of covering member 106 can be longitudinally compressed against the end(s) of endoprosthesis 104.

System 100 can comprise, for example, a catheter tip 108. In various embodiments, catheter tip 108 is positioned at a distal end of elongate member 102 and distal to a distal end of endoprosthesis 104. Catheter tip 108 can comprise a distal end 118 having a tapered profile. In various embodiments, catheter tip 108 further comprises a proximal end 120.

In various instances, system 100 further comprises an end cap 110. End cap 110 may prevent covering member 106 from hanging-up on the endoprosthesis during deployment of endoprosthesis 104 (i.e., removal of the covering member from around endoprosthesis 104). End cap 110 can comprise, for example, a mildly or moderately deformable material, i.e., a low durometer polymeric material at least on the section closest to the endoprosthesis. For example, the low durometer polymeric material can have a durometer between 15 and 70 Shore on the Type A scale. In various embodiments, the end cap 110 can be constructed so as to be more compliant along the axis parallel to the longitudinal axis of the guiding member than across its radial dimension.

End cap 110 can comprise, for example, a cylindrical body 112. End cap 110 can be located distal and adjacent to a distal end of endoprosthesis 104. In various embodiments, endoprosthesis 104 can have a distal edge which can abut or be disposed adjacent to end cap 110. In various embodiments, end cap 110 is integral to catheter tip 108. In other embodiments, end cap 110 and catheter tip 108 are distinct elements and are not integral to each other. Further, end cap 110 and catheter tip 108 can be spaced apart from one another, such that there is a gap or space between proximal end 120 of catheter tip 108 and a distal end of end cap 110. Although end cap 110 will be described with relation to catheter tip 108 (i.e., proximal end 120 of catheter tip 108 will refer to both the proximal end of catheter tip 108 and end cap 110), any configuration of catheter tip 108 and end cap 110 is within the scope of the present disclosure.

End cap 110 can further comprise a region of reduced diameter 114. In various embodiments, region of reduced diameter 114 is located between distal end 118 and proximal end 120 of end cap 110. For example, region of reduced diameter 114 can comprise a cylindrical portion of end cap 110 that has a diameter less than that of cylindrical body 112.

In various instances, covering member 106 can extend beyond the distal end of endoprosthesis 104 and onto end cap 110. For example, the distal end of covering member 106 can be positioned along a region of reduced diameter 114. The covering member 106 may encase a region of reduced diameter 114 tightly and therefore have an effective constrained diameter towards the distal end 118 of end cap 110 that is less than an effective constrained diameter of the covering member 106 around a ridge 122. In various embodiments, a portion of the distal end of covering member 106 can comprise a diameter less than that of cylindrical body 112 and equal to or greater than that of region of reduced diameter 114. In such embodiments, the distal end of covering member 106 can be secured within region of reduced diameter 114 or perhaps along ridges 122, which may assist in maintaining the position of the distal end during delivery of endoprosthesis 104 and/or prevent premature or undesired retraction of the distal end of covering member 106.

With reference to FIGS. 1-3B, proximal end 120 of end cap 110 can further comprise a profile 116. In various embodiments, after deployment of endoprosthesis 104, catheter tip 108 and end cap 110 are retracted back into outer shaft 150. Profile 116 may assist in retracting catheter tip 108 and end cap 110. For example, profile 116 can comprise a taper which may facilitate retraction of catheter tip 108 back into outer shaft 150 by providing an angled face of proximal end 120 instead of a flat and/or square face of proximal end 120.

Figure 3A:
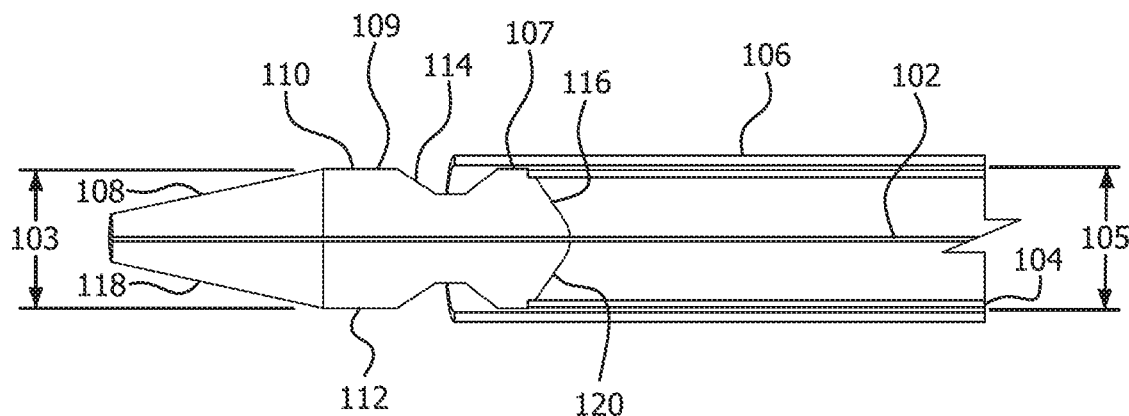
FIGS. 3A, 3B, and 3C illustrate partial cross sectional views of combined tips and end caps of endoprosthesis delivery systems in accordance with the present disclosure.
Figure 3B:
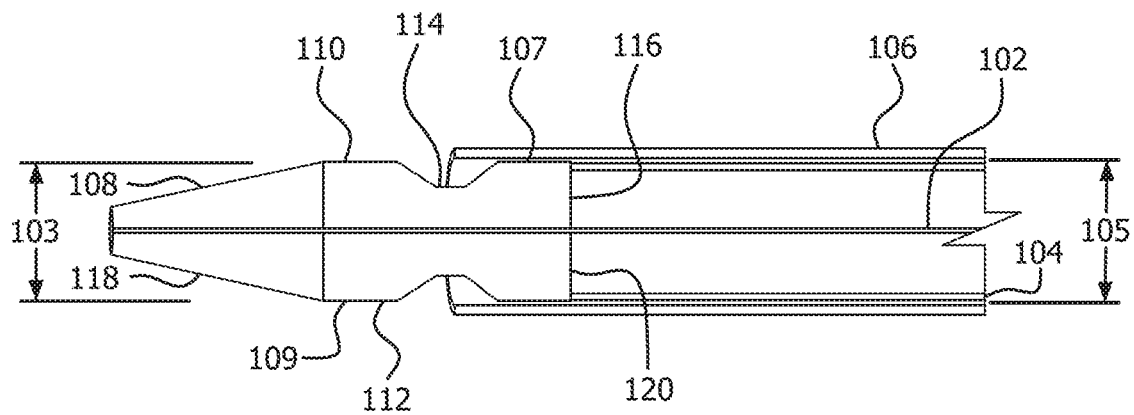

In certain instances, the end cap 110 may be described as including have various regions. For example, as shown in FIGS. 3A and 3B, the end cap 110 may have an end cap proximal region 107 and an end cap distal region 109. In some cases, as shown in FIGS. 3A and 3B, the end cap 110 may include an end cap reduced diameter region 114 between the end cap proximal region 107 and the end cap distal region 109. In addition, the end cap proximal region 107 may also include an end cap proximal region effective maximum diameter 105 and the end cap distal region 109 may include an end cap distal region effective maximum diameter 103.

Figure 3C:
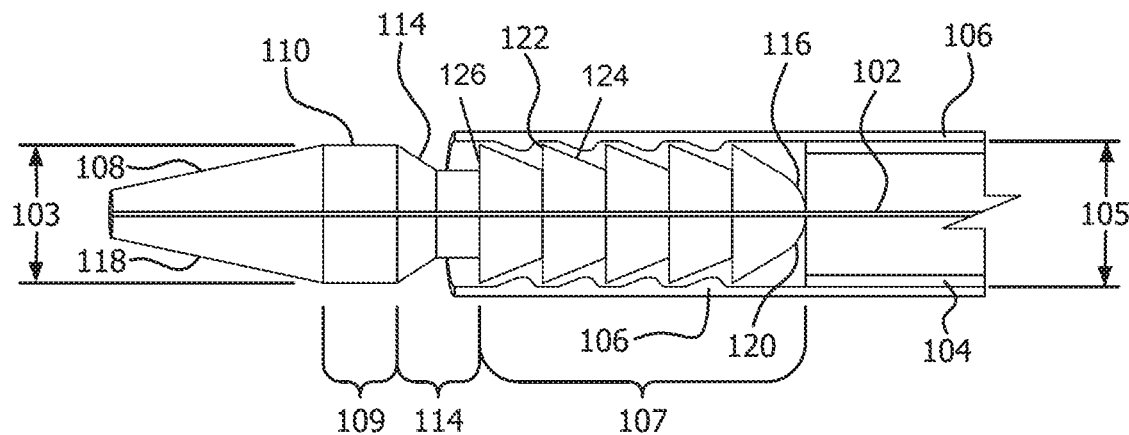

In certain instances, the end cap 110 may comprise various features. For example, as shown in FIG. 3C, the end cap 110 may comprise one or more (e.g., 2, 3, 4, 5, 6, or more) ridges 122. The ridges 122 may be in the end cap proximal region 107 as shown in FIG. 3C or they may exist in other regions, e.g., end cap distal region 109 or end cap reduced diameter region 114. The ridges 122 may taper between the maximum diameter 103 of the end cap 110 and the end cap reduced diameter region 114. The ridges 122 may have a perpendicular portion 126 and a tapered portion 124 to a center line of an elongate member (e.g., 102) as shown in FIG. 3C. The tapered portion 124 may form an angle between 5 and 45 degrees from a centerline (e.g., of endcap 110 or elongate member 102). For example, the tapered portion 124 may be approximately 5, 10, 15, 20, 25, 30, 35, 40, or 45 degrees depending on application. The tapered portion 124 may have a larger effective diameter towards the distal end 118 than the proximal end 120 of endcap 110 or alternatively the tapered portion 124 may have a larger effective diameter towards the proximal end 120 than the distal end 118. In addition, the ridges 122 may include rounded or flattened edges. The ridges 122 may have a flattened edge with a range of approximately 0.02 mm to 0.2 mm or more. For example, a ridge 122 may have a flattened edge of 0.02 mm, 0.06 mm, 0.12 mm, 0.14 mm, 0.16 mm, 0.18 mm or 0.2 mm. A ridge 122 may also have a rounded edge with a dimension ranging between approximately 0.02 mm and 0.4 mm. For example, a ridge 122 may have a rounded edge of approximately 0.02 mm, 0.05 mm, 0.08 mm, 0.11 mm, 0.14 mm, 0.17 mm, 0.20 mm, 0.23 mm, 0.26 mm, 0.29 mm, 0.32 mm, 0.35 mm, 0.038, 0.041 mm. The proximal end 120 of end cap 110 may abut the endoprosthesis 104. In certain instances, the endoprosthesis 104 may extend onto the proximal end 120 of endcap 110, and in other instances, the endoprosthesis 104 may extend up to the proximal end 120, as is shown in FIG. 3C. In certain instances, the ridges may be used to help a covering member 106 to resist movement. For example, when the endoprosthesis delivery system 100 is inserted through an introducer sheath or during manufacturing.

Figure 4A:
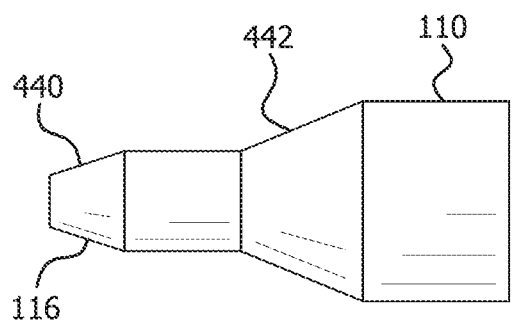
FIGS. 4A, 4B, and 4C illustrate side views of combined tips and end caps of endoprosthesis delivery systems in accordance with the present disclosure.
Figure 4B:
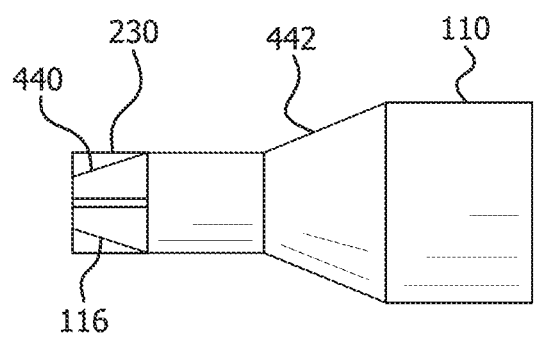
Figure 4C:
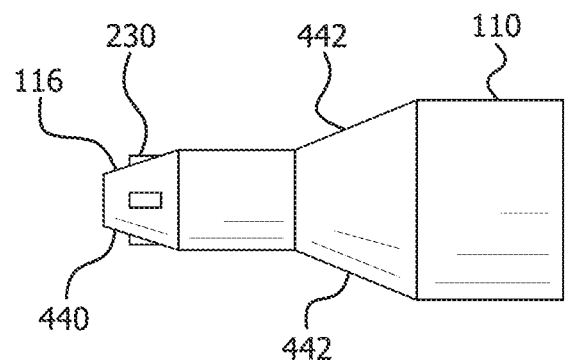

In certain instances, regions of the end cap can have various diameters. For example, as shown in FIGS. 3A-3C, the end cap proximal region 107 and the end cap distal region 109 have effective maximum diameters (105, 103) that are approximately equal. In FIGS. 4A-4C the end cap 110 has varying diameters. The ridges 122 may define the end cap proximal region maximum effective diameter 105. For example, as shown in FIG. 3C, the ridges 122, define the end cap proximal region maximum effective diameter 105. The end cap proximal region maximum effective diameter 105 may be the same dimension as a constrained endoprosthesis 104 maximum effective diameter.

As shown in FIGS. 3A-3C, the covering member 106 may extend along the endoprosthesis 104 and end cap proximal region 107. The covering member 106 may lie essentially parallel to elongate member 102. The covering member may partially lie between ridges 122. In other cases, the covering member 106 may taper from a larger diameter along the endoprosthesis 104 to a smaller diameter along end cap 110. The covering member 106 may be removed along end cap 110 and endoprosthesis 104, thereby exposing endoprosthesis 104 and thus allowing the endoprosthesis to be expanded. In some cases, the covering member 106 may more easily be removed along end cap 110 and along a constrained endoprosthesis 104 (e.g., an endoprosthesis with a scalloped distal end) if the maximum effective diameters of the end cap 110 and endoprosthesis 104 are approximately equal. The endoprosthesis 104 may have a graft portion and a stent portion. The endoprosthesis 104 may also include stent portions that extend beyond the graft portion. These stent portions may include various shapes, such as scalloped ends. In other cases, it may be beneficial to have constrained endoprosthesis 104 have an effective maximum diameter that is greater than the effective maximum diameter of the end cap 110.

Profile 116 can comprise, for example a continuous taper. In other embodiments, with initial reference to FIG. 4A, profile 116 can comprise a "staged" taper. For example, profile 116 can comprise one or more tapered segments 440 and 442. Tapered segments 440 and 442 can be separated by one or more non-tapered segments. Profiles 116 comprising any configuration and number of tapered segments are within the scope of the present disclosure.

In various embodiments, end cap 110 can further comprise one more fins 230. In such embodiments, fins 230 are positioned at the proximal end 120. For example, one or more fins 230 can be located along profile 116 of proximal end 120. In various embodiments, fins 230 can comprise a protrusion from profile 116. For example, as end cap 110 and catheter tip 108 are retracted into outer shaft 150, the proximal end of outer shaft 150 can exert pressure on fins 230, causing them to fold over. By at least partially folding over, fins 230 may reduce the difficulty in retracting catheter tip 108 and end cap 110 back into outer shaft 150.

In various embodiments, fins 230 may provide a resistance to radial forces against an outer surface of end cap 110. For example, fins 230 may be subjected to a radial compressive force by endoprosthesis 104 and/or covering member 106. Fins 230 may resist such compressive forces and maintain a relatively constant diameter. In various embodiments, characteristics of fins 230 such as thickness, material, and length, among others, may be selected to provide sufficient resistance to radial forces while maintaining the ability of the fins to fold over when retracted into outer shaft 150.

With initial reference to FIGS. 4B and 4C, fins 230 can be positioned on end cap 110 in various configurations. For example, as illustrated in FIG. 4B, fins 230 can traverse the length of the taper of profile 116. In other embodiments, as illustrated in FIG. 4C, fins 230 can be positioned along a portion of the length of the taper of profile 116 (instead of the entire length of the taper). Further, fins 230 can be positioned in any combination of arrangements, including one or more fins 230 located along one or more different portions of the length of the taper of profile 116. Any positioning of fins 230 along profile 116, including combinations of different positions, is within the scope of the present disclosure.

In various embodiments, fins 230 can have the same or nearly the same diameter as cylindrical body 112. Such fins 230 can provide a constant diameter, and therefore a consistent surface of support, for covering member 106. For example, as illustrated in FIG. 4C, fins 230 may comprise a diameter less than the diameter of cylindrical body 112. Although described as having the same diameter as cylindrical body 112, fins 230 can comprise any suitable diameter, including multiple portions or regions having different diameters.

Figure 5:
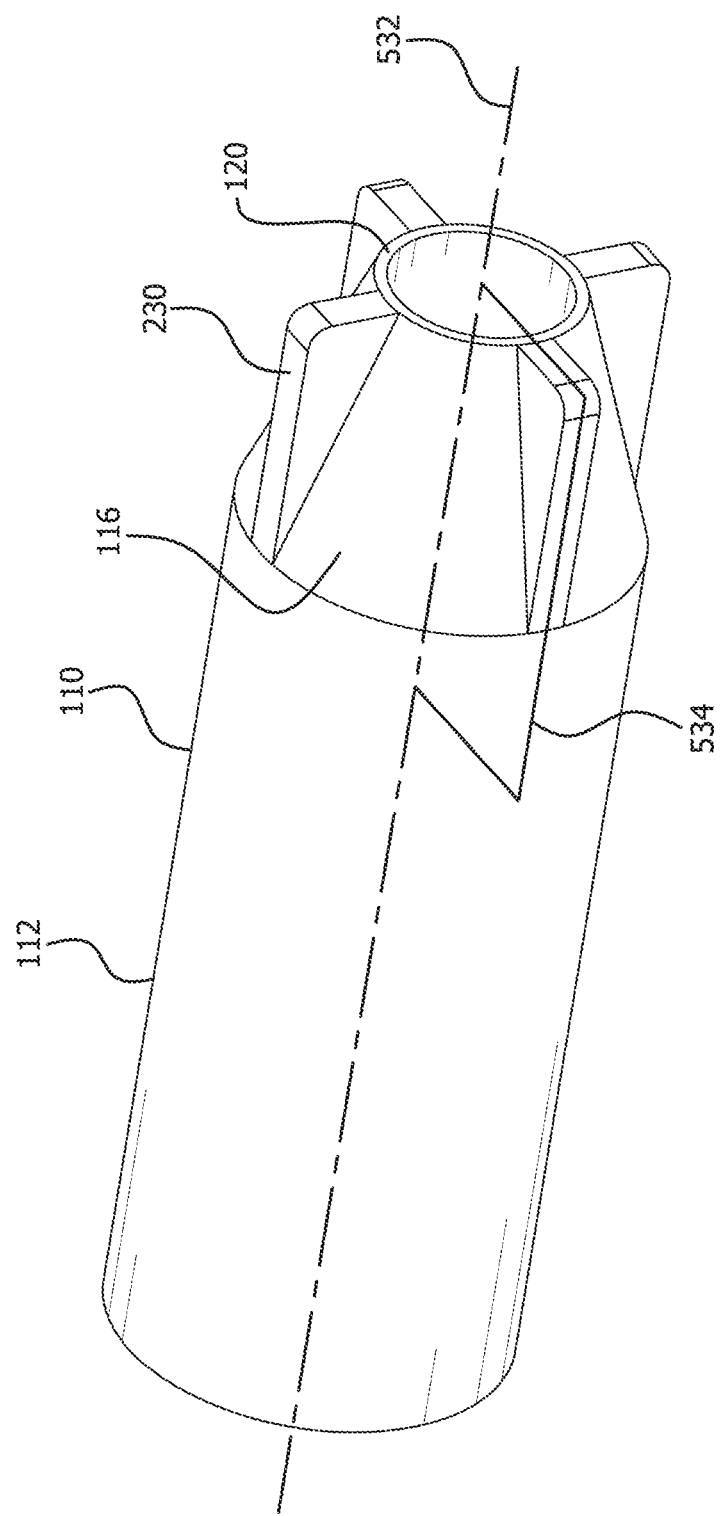
FIG. 5 illustrates a magnified perspective view of a portion of an end cap of an endoprosthesis delivery system in accordance with the present disclosure.

With initial reference to FIG. 5, multiple fins 230 located at proximal end 120 of end cap 110 are illustrated. For example, to assist in understanding the spatial relationship and orientation of fins 230 and end cap 110, end cap 110 can comprise a longitudinal axis 532. In various embodiments, fins 230 are oriented such that a plane 534 parallel to fin 230 is parallel to and intersects with a portion of the length of longitudinal axis 532. Stated another way, in such embodiments, fins 230 are generally "straight" relative to longitudinal axis 532.

Figure 6:
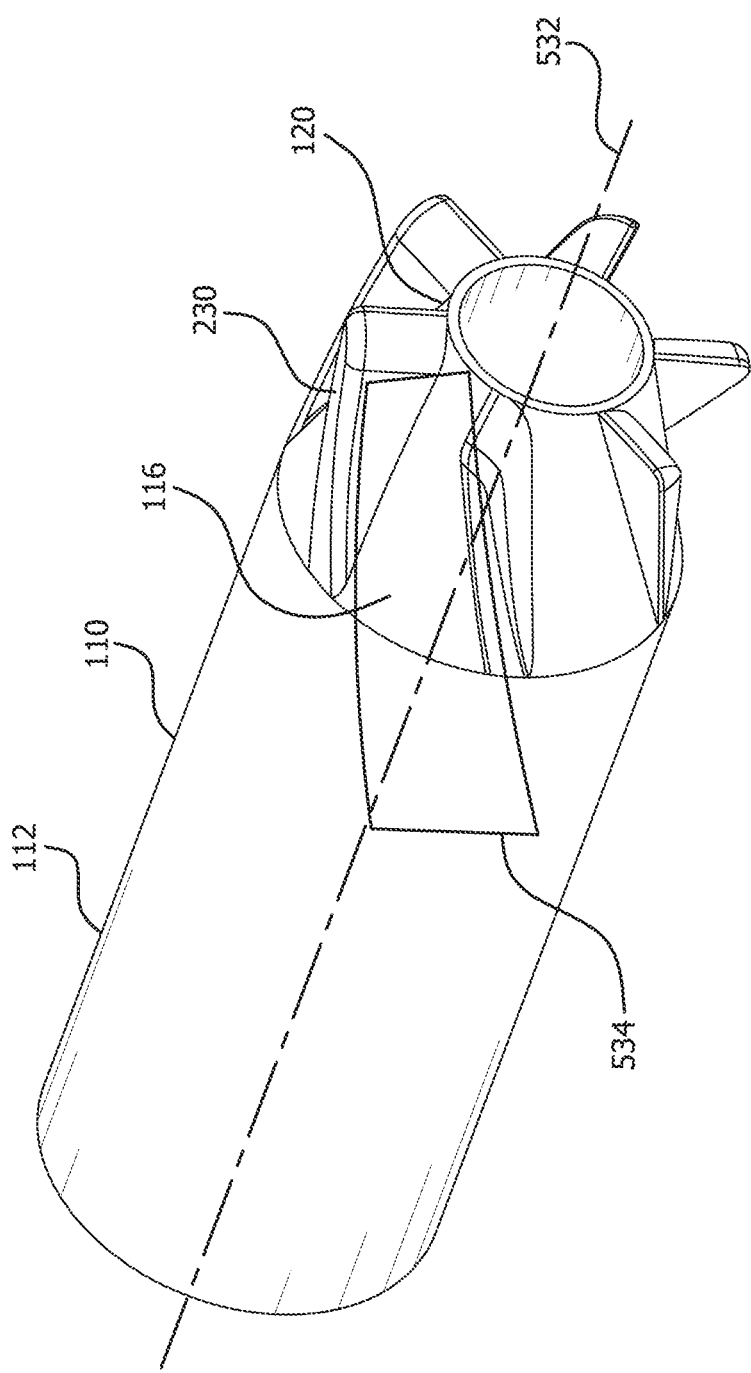
FIG. 6 illustrates a magnified perspective view of a portion of an end cap of another endoprosthesis delivery system in accordance with the present disclosure.

With initial reference to FIG. 6, multiple fins 230 located at proximal end 120 of end cap 110 are illustrated. In various embodiments, fins 230 are oriented such that a plane 534 parallel to fin 230 is non-parallel to and intersecting at a point with longitudinal axis 532. Stated another way, in such embodiments, fins 230 are generally "angled" relative to longitudinal axis 532.

Although described in connection with two specific examples (e.g., the "straight" fins of FIG. 5 and the "angled" fins of FIG. 6), fins 230 can be configured in any way that provides support to covering member 106 at proximal end 120 of end cap 110. For example, fins 230 can be curved, bent, or otherwise non-straight. Any suitable configuration of fin 230 is in accordance with the present disclosure.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

Further, any combination of the elements and components of the present disclosure is within the scope of the present invention. Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

What is claimed is:
1. An endoprosthesis delivery system comprising:
   an elongate member having a proximal end and a distal end, the elongate member being configured to support an endoprosthesis proximal to its distal end; and
   an end cap having a proximal end and a distal end, the proximal end of the end cap including a section having a reduced profile, wherein the reduced profile includes a protrusion that is configured to support a covering member surrounding the endoprosthesis and has a relatively constant diameter that is the same or nearly the same as a diameter of the proximal end of the end cap;

wherein the end cap is coupled to the elongate member such that the proximal end of the end cap is adjacent and distal to the distal end of the elongate member.

2. The endoprosthesis delivery system of claim 1, wherein the reduced profile includes a taper that decreases in diameter proximally.

3. The endoprosthesis delivery system of claim 1, wherein the protrusion is a fin.

4. The endoprosthesis delivery system of claim 3, wherein the fin has a length, a width, and a height.

5. The endoprosthesis delivery system of claim 4, wherein the length of the fin corresponds to a length of the section having the reduced profile.

6. The endoprosthesis delivery system of claim 4, wherein a length of the section having the reduced profile exceeds the length of the fin.

7. The endoprosthesis delivery system of claim 4, wherein the height of the fin corresponds to a diameter of the end cap in a region distal to the section having the reduced profile.

8. The endoprosthesis delivery system of claim 4, wherein the fin is curved, bent, or otherwise non-straight along its length.

9. The endoprosthesis delivery system of claim 3, wherein the fin is straight relative to a longitudinal axis of the end cap.

10. The endoprosthesis delivery system of claim 9, wherein the fin extends along the section having the reduced profile such that that a plane parallel to the fin is parallel to and intersects with the longitudinal axis of the end cap.

11. The endoprosthesis delivery system of claim 3, wherein the fin is angled relative to a longitudinal axis of the end cap.

12. The endoprosthesis delivery system of claim 11, wherein the fin extends along the section having the reduced profile such that that a plane parallel to the fin is non-parallel with and intersects with the longitudinal axis of the end cap.

13. The endoprosthesis delivery system of claim 3, wherein the end cap includes a plurality of fins.

14. The endoprosthesis delivery system of claim 3, further comprising an outer shaft, and wherein the fin is configured to deflect upon retraction of the end cap into the outer shaft.

15. The endoprosthesis delivery system of claim 14, wherein the fin is configured to fold upon retraction of the end cap into the outer shaft.

16. The endoprosthesis delivery system of claim 1, wherein the section having the reduced profile includes a plurality of ridges that define the protrusion.

17. An endoprosthesis delivery system comprising:
an elongate member;
an endoprosthesis disposed about the elongate member; and
an end cap positioned such that a proximal end of the end cap is distal to a distal end of the endoprosthesis;
wherein the proximal end of the end cap comprises a section having a reduced profile, and wherein the reduced profile includes a protrusion that has a relatively constant diameter that is the same or nearly the same as a diameter of the proximal end of the end cap and is configured to deflect to allow for retraction of the end cap into an outer shaft.

18. The endoprosthesis delivery system of claim 17, wherein the reduced profile includes a taper that decreases in diameter proximally.

19. The endoprosthesis delivery system of claim 17, wherein the protrusion is a fin.

20. The endoprosthesis delivery system of claim 19, wherein the fin has a length, a width, and a height.

21. The endoprosthesis delivery system of claim 20, wherein the length of the fin corresponds to a length of the section having the reduced profile.

22. The endoprosthesis delivery system of claim 20, wherein a length of the section having the reduced profile exceeds the length of the fin.

23. The endoprosthesis delivery system of claim 20, wherein the height of the fin corresponds to a diameter of the endoprosthesis when constrained in a delivery configuration.

24. The endoprosthesis delivery system of claim 20, wherein the fin is curved, bent, or otherwise non-straight along its length.

25. The endoprosthesis delivery system of claim 19, wherein the fin is straight relative to a longitudinal axis of the end cap.

26. The endoprosthesis delivery system of claim 25, wherein the fin extends along the section having the reduced profile such that that a plane parallel to the fin is parallel to and intersects with the longitudinal axis of the end cap.

27. The endoprosthesis delivery system of claim 19, wherein the fin is angled relative to a longitudinal axis of the end cap.

28. The endoprosthesis delivery system of claim 27, wherein the fin extends along the section having the reduced profile such that that a plane parallel to the fin is non-parallel with and intersects with the longitudinal axis of the end cap.

29. The endoprosthesis delivery system of claim 19, wherein the end cap includes a plurality of fins.

30. The endoprosthesis delivery system of claim 19, wherein the fin is configured to fold upon retraction of the end cap into the outer shaft.

31. The endoprosthesis delivery system of claim 17, wherein the section having the reduced profile includes a plurality of ridges that define the protrusion.

32. The endoprosthesis delivery system of claim 17, wherein the endoprosthesis is a stent.

33. The endoprosthesis delivery system of claim 17, wherein the endoprosthesis is a stent-graft.

* * * * *